(12) United States Patent
Stevenson et al.

(10) Patent No.: US 7,983,763 B2
(45) Date of Patent: Jul. 19, 2011

(54) IMPLANTED LEAD SLEEVE HAVING RFID TAG

(75) Inventors: Robert A. Stevenson, Canyon Country, CA (US); Christine A. Frysz, Orchard Park, NY (US); Geddes Frank Tyers, Vancouver, CA (US); Buehl E. Truex, Glendora, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 12/845,559

(22) Filed: Jul. 28, 2010

(65) Prior Publication Data

US 2010/0331932 A1 Dec. 30, 2010

Related U.S. Application Data

(63) Continuation-in-part of application No. 11/943,470, filed on Nov. 20, 2007, now Pat. No. 7,787,958.

(60) Provisional application No. 61/243,084, filed on Sep. 16, 2009.

(51) Int. Cl.
*A61N 1/00* (2006.01)

(52) U.S. Cl. ...................................................... 607/115
(58) Field of Classification Search ................... 607/115
See application file for complete search history.

(56) References Cited

U.S. PATENT DOCUMENTS

2001/0000187 A1* 4/2001 Peckham et al. ............... 607/48

* cited by examiner

*Primary Examiner* — George Manuel
(74) *Attorney, Agent, or Firm* — Kelly Lowry & Kelley, LLP; Scott W. Kelley; Michael F. Scalise

(57) ABSTRACT

An identification device for an implantable lead includes an associated implantable sleeve and a radio frequency identification device (RFID) tag associated with the sleeve. The RFID tag includes information relating to the implantable lead, its associated lead system, or an associated implantable medical device. The RFID tag may be hermetically sealed within the sleeve and the sleeve selectively fixed along a length of the lead. The sleeve may comprise a loop forming an aperture, a crimped clamp device, a clamp device including a ratchet, clip, or rivet mechanism, or a clamp device including two separate clamshells, all of which allow for secure attachment to the lead. Alternatively, the sleeve may integrally be formed as part of the lead between a lead conductor and an insulated lumen. An external interrogator may be used for identifying information contained within the RFID tag.

19 Claims, 7 Drawing Sheets

IMPLANTED LEAD SLEEVE HAVING RFID TAG

BACKGROUND OF THE INVENTION

The present invention generally relates to identification of implanted leads, such as of an implantable medical device (IMD). More particularly, the present invention relates to implanted lead sleeves having RFID tags associated therewith.

It would be beneficial if physicians were able to obtain additional information about an implanted device and/or a patient from an implanted identification tag. Such information would preferably include, in addition to the manufacturer and model number of the device, the serial number of the device, the date of manufacture, the treating physician's name and contact information and, if authorized by the patient, the patient's name, contact information, medical condition and treatment, and other relevant information concerning device programmed parameters and the like. There are many potential benefits from being able to determine the specific model and serial number and additional related device or patient information in an implanted medical device or associated lead system. For example, product recalls are an increasingly complex and extensive problem, and the ability to rapidly identify the precise model and serial number of an implanted product may be life-saving. Cost savings for the involved company may also be substantial. Such implanted products may be either passive or active, and include things like stents, heart valves, neoplant hardware, and hip implant hardware or the like. They may also include external devices like Holter monitors, external pacemakers, and so forth.

Currently, most IMD patients carry some sort of identification. This may be in the form of a card carried in the wallet or an ID bracelet indicating, for example, that the patient is a pacemaker wearer of a certain model and serial number. However, such forms of identification are often missing or not up to date. In addition, manufacturers' databases and related patient cardiac rhythm management device (CRMD) system cards are frequently incomplete and/or inaccurate. It is quite common for an elderly patient to be presented at the emergency room (ER) of a hospital without his or her wallet and without wearing or carrying any type of a bracelet or other identification. In addition, there have been a number of situations where the patient (due to dementia or Alzheimer's, etc.) cannot clearly state that he or she even has a pacemaker.

There are known in the art various methods for identifying implanted medical devices. One such method is the use of X-ray identification tags encapsulated within header blocks of cardiac pacemakers or implantable cardioverter defibrillators (ICDs). Such X-ray identification tags can be read on an X-ray of the implanted device and provide information to the physician. The information so provided is very limited due to space and typically includes only the manufacturer or the model number of the implanted device. In an emergency, the time delay to obtain X-ray films can also be problematic.

Oftentimes the ER physician will palpitate the patient's chest and feel that there is an implanted device present. If the patient is comatose, has low blood pressure, or is in another form of cardiac distress, this presents a serious dilemma for the physician. At that moment, all that the physician knows is that the patient has some sort of IMD implant. It could be a pacemaker, a cardioverter defibrillator (ICD), a vagus nerve stimulator, a deep brain stimulator or other type of neurostimulator, or a variety of other therapeutic and/or monitoring devices. What happens next is both laborious and time consuming. The ER physician will have various manufacturers' cardiac rhythm management device (CRMD) programmers transported from the hospital pacemaker or ICD follow-up clinic or other site down to the ER. ER personnel will then try to interrogate the implantable medical device to see if they can determine what it is. For example, they might first try to use a Medtronic programmer to see if it is a Medtronic pacemaker. If unsuccessful, they might try a St. Jude, a Guidant, an ELA, a Biotronik or one of a number of other programmers that may be available. If none of those programmers work, then the ER physician has to consider that the implanted device may be a neurostimulator and perhaps secure a Cyberonics or Neuropace programmer. It may also be that the telemetry programming wand is mal-positioned as this can be quite sensitive or that the implanted device has failed, etc.

It would be a great advantage and potentially lifesaving if the ER physician (or ambulance emergency medical technician) could very quickly identify, at a minimum, the type of implant, manufacturer and model number using a generic RFID reader. In certain cases, for example, with a pacemaker patient who is in cardiac distress, quickly identifying and obtaining the appropriate external programmer could allow the ER physician or other trained personnel to boost the pacemaker output voltage and/or pulse rate to properly recapture the heart, obtain a regular rhythm and stabilize blood pressure. A variety of other programmable stabilizing adjustments may also be made as required. All of the time lost while trying to identify the right programmer can be detrimental not only to the patient, but also detract attention from other critical tasks for that patient and for other patients in the ER. Accordingly, there is a need for a way to rapidly identify the type and model number of all IMD so that the proper external programmer for it can be rapidly identified and obtained, and/or other appropriate activities initiated. The teachings of U.S. Patent Application Publication No. US 2006/0212096 A1 are incorporated herein by reference.

It is also important to note that pulse generator or IMD lead systems generally remain in the human body much longer than the IMD itself. For example, in the case of a cardiac pacemaker, the pulse generator power cell (battery) may last for three, five or even up to 10 years depending on a variety of program settings and other features, whereas leads (the insulative conductors connecting the pulse generators to the heart) typically have a very low failure rate even after 10 years in the human body. Changing the pulse generator is, from a technical perspective, a relatively minor procedure whereas the removal of leads from the heart, once they have been implanted for greater than six months to a year, requires relatively sophisticated equipment and surgical skill and is considerably more risky for the patient. This is because the lead insulation tends to become embedded and overgrown by scar tissue. This can involve the whole length of the lead and tends to be particularly dense in the great veins, adjacent to a heart valve and adjacent to electrodes. Thus, on occasion, even open heart surgery may be required to remove lead systems. In contrast, when a pacemaker is replaced, the tissue over the pulse generator is simply incised, the old pulse generator disconnected and the existing lead plugged into the new pacemaker.

Unfortunately, it is not uncommon for leads to fail for various reasons. They could fail due to breakdown of the insulation, fracture of the conductor, etc. Leads may also be abandoned because they have migrated to an improper position within the heart, etc. When a lead is abandoned, the physician normally snips off the connectors and tags the remnants in the adjacent tissue. New leads are then implanted often in parallel with the old abandoned leads. Abandoned leads are often well tolerated, but there is also extensive literature on the complications they can cause, including venous obstruction, infection, tachyarrhythmias, damage during MRI procedures and many others.

For example, it has been demonstrated in the literature that during an MRI procedure, leads (abandoned or live) can greatly overheat due to the powerful RF and magnetic fields induced during MRI. Accordingly, it is important that there be a way of identifying not only the presence of abandoned leads, but also the precise lead type and model. This applies not only during follow-up of complex patients (and they are common), but also when device patients are presented to an Emergency Room under various circumstances. Regardless of the circumstances under which a medical practitioner may contemplate performing a medical diagnostic procedure on the patient such as MRI, that patient, and in fact, all patients, will be well served by caregivers being able to rapidly and efficiently identify the make and model number of all IMDs, all leads and other components, like adapters, and all other implanted foreign materials whether functioning or abandoned. In addition, such technology should also improve the efficiency of product recall management.

It is also important to note that certain lead systems are evolving to be compatible with specific types of medical diagnostic procedures. For example, US 2009/0163981 A1 and US 2006/0247684 A1, both of which are herein incorporated by reference, disclose the use of bandstop (tank) filters placed in series with leads or circuits of active medical devices to enhance their MRI compatibility. MRI systems vary in static field strength from 0.5 Tesla all the way to above 10 Tesla. A very popular MRI system, for example, operates at 3 Tesla and has a pulsed RF frequency of 128 MHz. There are specific certain lead systems that are evolving in the marketplace that would be compatible with only this type of MRI system. In other words, it would be dangerous for a patient with a lead designed for 3 Tesla to be exposed to a 1.5 Tesla system. Thus, there is also a need to identify such lead systems and their associated IMDs for medical personnel (such as the MRI technician or radiologist) when necessary, and to warn against potential highly dangerous therapeutic and diagnostic interventions. Therefore, there is a need to associate an RFID tag with both the IMD and its associated leads. For example, a patient that has a lead system that has been specifically designed for use with a 3 Tesla MRI system may have several pacemaker replacements over the years. It is important that the replacement pacemakers be 3 Tesla compatible and be compatible with the leads if the patient is to safely receive an MRI scan.

Accordingly, there is a continuing need for methods and means for associating RFID tags with IMDs, and particularly implanted leads thereof. Moreover, there is a continuing need for associating RFID tags with abandoned leads. There is further a continuing need to provide effective means for associating such RFID tags or other identifiers to such leads. The present invention fulfills these needs and provides other related advantages.

SUMMARY OF THE INVENTION

The identification device for an implantable lead includes an implantable sleeve associated with the implantable lead. A radio frequency identification device (RFID) tag is associated with the sleeve. The RFID tag includes information relating to the implantable lead, its associated lead system, or an associated implantable medical device (IMD). The RFID tag may be hermetically sealed within the sleeve and the sleeve selectively fixed along a length of the lead.

In an exemplary embodiment, the sleeve comprises a loop forming an aperture, where the aperture captures a portion of the lead therein. In another exemplary embodiment, the sleeve comprises a crimped clamp device for secure attachment to the lead. In another exemplary embodiment, the sleeve comprises a clamp for secure attachment to the lead including a ratchet, clip, or rivet mechanism. The clamp may comprise two separate clamshells configured to cooperatively capture the lead. In another exemplary embodiment, the sleeve is integrally formed as part of the lead, wherein the sleeve is disposed between a lead conductor and an insulated lumen.

An external interrogator may be used for identifying information contained within the RFID tag when brought into close proximity. The interrogator may be operably coupled to an access or reading device which can relay the information to a physician or access a database to retrieve a patient's information. The information may comprise a patient's name, a date of birth, a patient hospital identification number, a physician name, a medical history, a name and number of implanting physician, an implant date, an implant hospital, a lead model or serial numbers, a lead position, a defibrillation energy, a HV impedance, a P/R wave amplitude slew rate, a pacing threshold, a pulse pacing width, a pacing impedance, or a threshold current.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE INVENTION

As shown in the accompanying drawings, for purposes of illustration, the present invention is directed to identification of lead wires of an implantable medical device IMD. The present invention further relates to means for associating the RFID tag with the lead wire, such as an implanted lead sleeve, or a strap clip feature.

Figure 1:
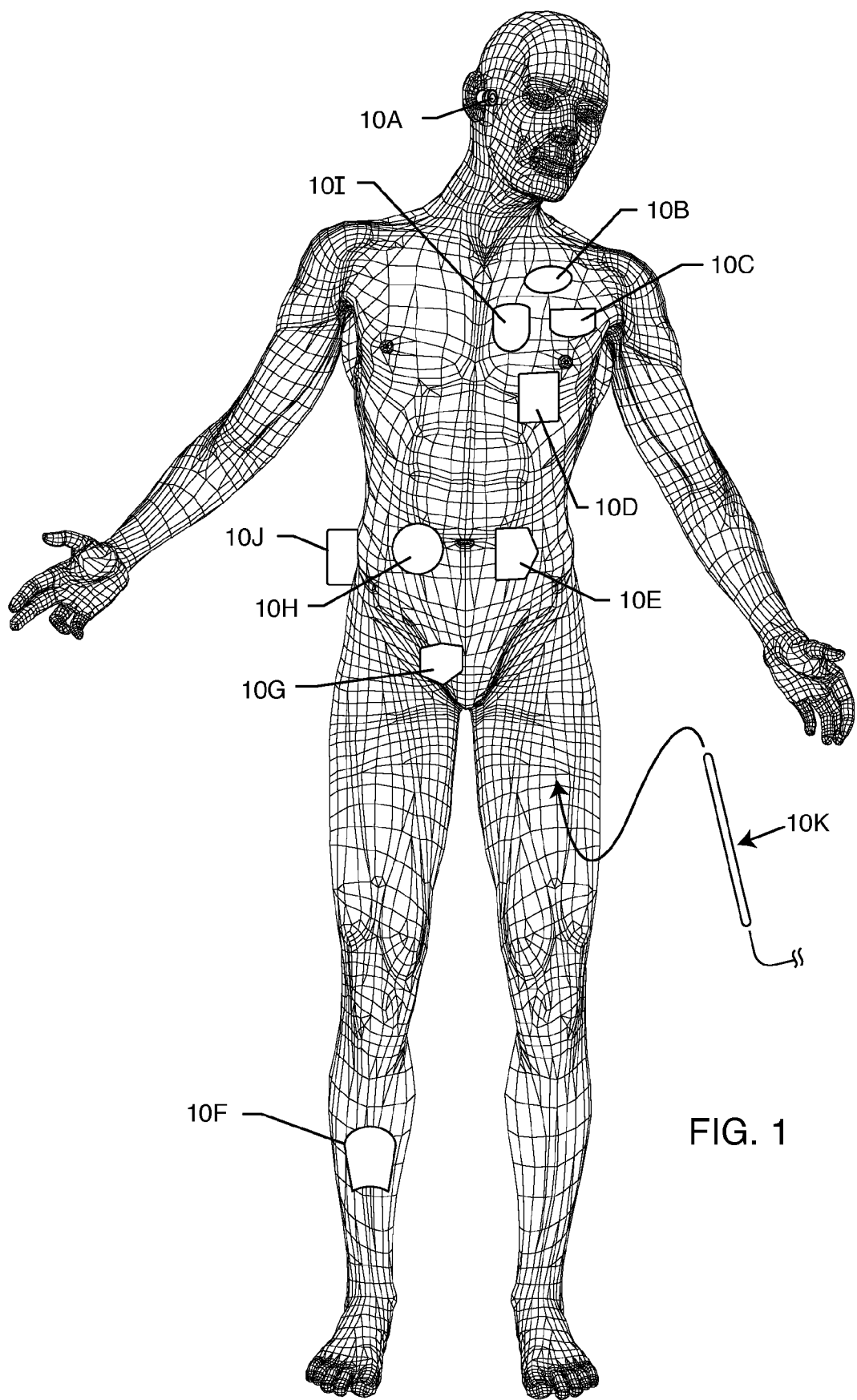
FIG. 1 is a wire-form diagram of a generic human body showing a number of implantable medical devices (IMDs) and associated internal and external lead wires.

FIG. 1 is a wire formed diagram of a generic human body. Various locations are shown for active, passive, structural and other implantable and external medical devices 10 that are currently in use, and in which the present invention may find application. 10A represents a family of external and implantable hearing devices which can include the group of hearing aids, cochlear implants, piezoelectric sound bridge transducers and the like. 10B includes an entire variety of neurostimulators and brain stimulators, and hydrocephalic fluid pumps, drug and hormone insulin injection administration devices, etc. 10C shows a cardiac pacemaker which is well-known in the art. 10D includes the various types of left ventricular assist devices (LVAD's), and artificial hearts, for example, the recently introduced centrifugal empowered devices. 10E includes an entire family of drug pumps which can be used for dispensing of insulin, chemotherapy drugs, pain medications and the like. 10F includes a variety of external or implantable bone growth stimulators for rapid healing of fractures. 10G includes urinary and/or fecal incontinence devices. 10H includes the family of pain relief spinal cord stimulators and anti-tremor stimulators. 10H also includes an entire family of other types of neurostimulators used to block pain. 10I is representative of implantable cardioverter defibrillators (ICDs) including those with biventricular and multi-site synchronization capabilities for the treatment of congestive heart failure (CHF). 10J illustrates an externally worn device. This external pack could be an insulin or other drug pump, an external neurostimulator or pain suppression device, a Holter monitor with skin electrodes or even a ventricular assist device power pack. While the model and serial number and date of manufacture could be obvious on the surface of an external module, much more detailed information could be included in/on an RFID chip. 10K illustrates the insertion of transcutaneous probe or catheter. These devices can be inserted into the femoral vein, for example, or into many other endovascular or endothelial lined cavities in the human body.

Figure 2:
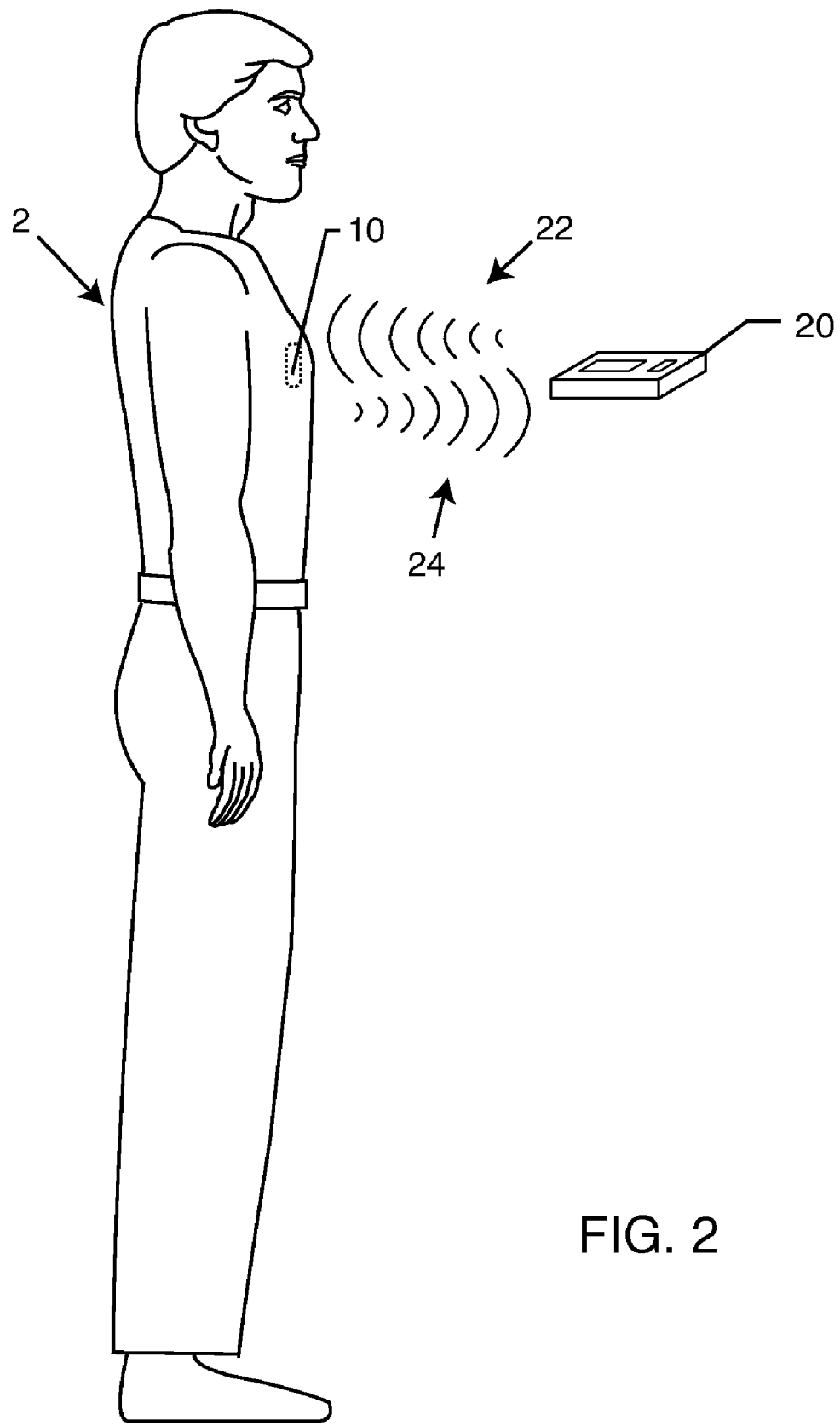
FIG. 2 is a depiction of a patient with an IMD, or associated lead wire, fitted with an RFID tag of the present invention and an external interrogator/reader.

FIG. 2 is an outline drawing of an adult male pacemaker patient with an IMD 10. FIG. 2 shows a dashed ellipse which indicates one potential location for an IMD 10. The location shown in FIG. 2 is typical of a right or left pectoral muscle implant. Right and left pectoral muscle implants are typical for a cardiac pacemaker or implantable cardioverter defibrillator (ICD). The right and left pectoral muscle region is chosen due to the easy access to the subclavian veins for insertion of lead wires and electrodes down into the heart. The present invention may also find application in other IMDs such as those described above and illustrated in FIG. 1.

FIG. 2 illustrates an RFID communicator 20, sometimes referred to as an interrogator or a reader, which sends an interrogation signal 22 to the IMD 10, or lead wires in patient 2. When an RFID tag is identified, the RFID tag sends a responding signal 24. Information can be obtained from the RFID tag, or information can be written thereto in volatile memory.

Figure 3:
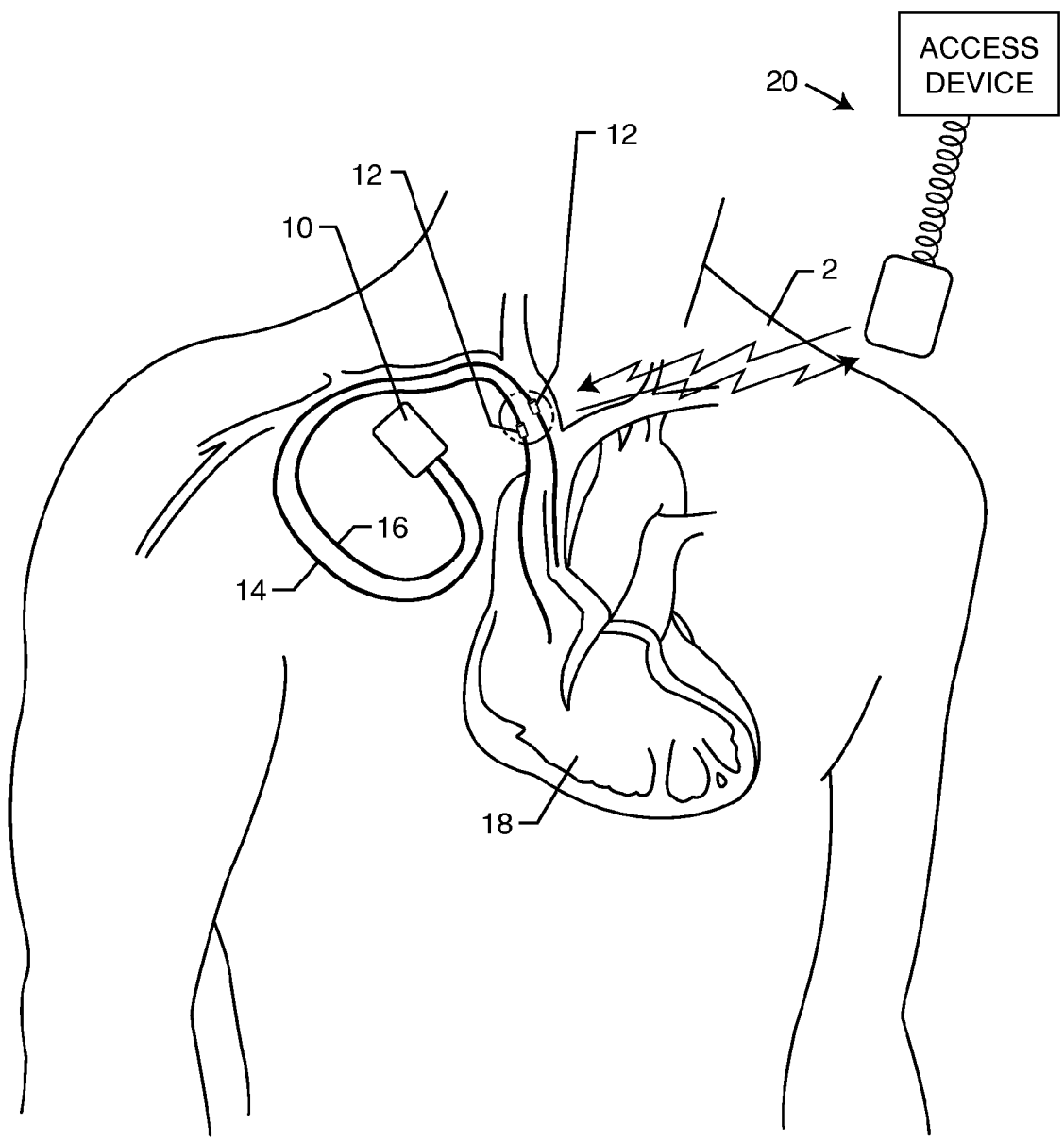
FIG. 3 is a perspective and somewhat schematic view of an implantable medical device (IMD) including lead wires directed to a heart of a patient, and an interrogator device for reading information from RFID tags associated with the lead wires, in accordance with the present invention.

FIG. 3 illustrates another view of the patient 2 having the IMD 10 implanted therein and being interrogated by a reader device 20. The IMD 10 has lead wires 14 and 16 extending therefrom and to a point in the patient's body necessary to receive signals, apply electrical shock, or other therapy, as is known in the art. In this case, the lead wires 14 and 16 comprise the lead system extending from the active implanted medical device 10 into the heart 18 of the patient 2. As described above, it is important that not only the medical device be identified, but also the lead wires 14 and 16. This is typically the case whether the lead wires 14 and 16 are operably connected to an IMD 10, or the IMD 10 has been removed and the lead wires 14 and 16 abandoned within the patient 2. Although a physician may be able to palpitate the patient 2 in an emergency situation and determine the presence of an implantable medical device 10, such is usually not the case with abandoned lead wires 14 and 16.

In accordance with the present invention, RFID tags 12 are associated with the one or more lead wires 14 and 16, so as to identify the presence of the lead wires 14 and 16 when a reader or interrogator 20 is brought in to sufficiently close proximity thereto. The interrogator or reader 20 may be operably coupled to an access or reading device, such as a computer, which can visually, or otherwise, relay information to the physician, access databases to retrieve patient information, and the like. The RFID chip within the RFID tag 12 preferably includes information about the patient, the IMD 10, and/or the lead wires 14 and 16. In a particularly preferred embodiment, the RFID tag 12 can store and transmit the patient's name and date of birth, the patient hospital identification number or physician name, and medical history. Preferably, the name and phone number of the implanting physician is given. The implant date and the hospital are also preferably given. Moreover, information regarding the implanted device 10, the lead wire model numbers or serial numbers, and the lead wire positions (e.g. RV, RA, LV) are also provided. The defibrillation energy, HV impedance (ohms), P/R Wave amplitude slew rate, pacing threshold, pulse pacing width, pacing impedance (ohms), threshold current (ma), and other such information may also be stored on the RFID tag for assisting the physician in determining treatment parameters. Merely knowing about the presence of the lead wires 14 and 16, and/or the implantable medical device 10, also alerts the physician to the limitations of conducting an MRI on the patient.

With reference now to FIGS. 4-9, it is important that the RFID tag 12 be hermetically sealed such that body fluids do not enter therein and render the RFID tag 12 inoperable. This may be done in a variety of ways. For example, the RFID tag 12 may be hermetically sealed within a container. Projections extending from the container, such as a loop, creating an aperture, can be used to attach the container to tissue immediately adjacent to one of the lead wires 14 and/or 16, directly to the lead wire 14 and/or 16, or the like. The RFID tag, such as in the container, may also be injected into the body tissue.

Figure 4:
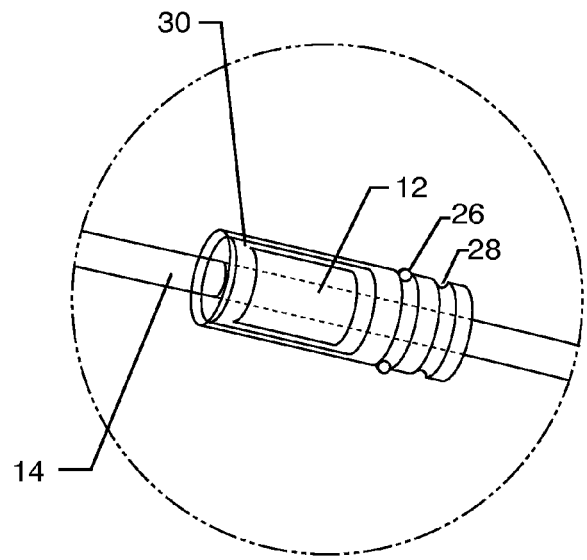
FIG. 4 is an enlarged view of the lead wire of FIG. 3, illustrating the attachment of an RFID tag thereto.

The RFID tag 12 can also be directly attached to the lead wire 14 or 16, or formed as a part thereof during the manufacture of the lead wire. For example, as illustrated in FIG. 4, the RFID tag 12 is disposed within a hermetically sealed encapsulant material or the like 30 which is fixed to the exterior of the lead wire 14, as illustrated in FIG. 4. A suture 26 can wrap or connect around a channel 28 such that the RFID tag 12 can be attached, affixed, or anchored to bodily tissue.

Figure 5:
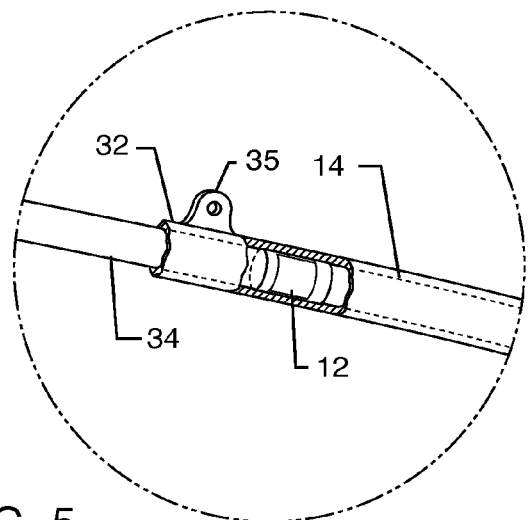
FIG. 5 is an enlarged view similar to FIG. 4, but illustrating another method of attachment of the RFID tag to the lead wire.

The RFID tag 12 may also be disposed within the insulation 32 surrounding the lead wire 14 so as to be disposed between the lead body containing conductive wire(s) 34 and the outer insulated sheet 32, as illustrated in FIG. 5. It will be appreciated that additional sheets or layers of non-conductive material may be placed between the lead body/conductive wire 34 and the RFID tag 12, and even between the RFID tag 12 and the outer sheets 32 so as to create an electrical insulation and isolation of the RFID tag 12 and the electrical wire 34, while still hermetically sealing the RFID tag 12 within the lead wire 14. An optional tissue suture tab (or tabs) 35 may be included so that the RFID tag assembly 32 and lead 34 may be affixed/anchored to body tissue.

Figure 6:
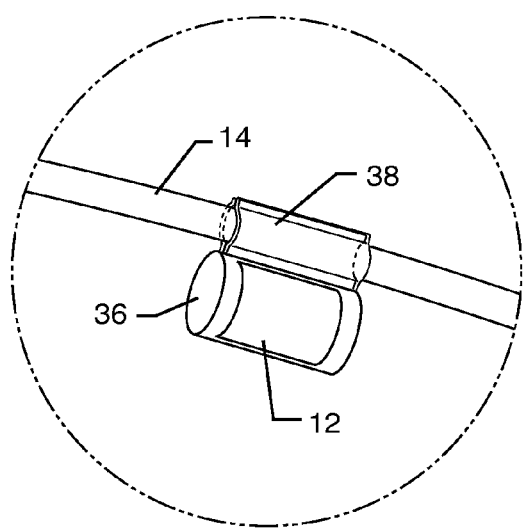
FIG. 6 is yet another enlarged view of an RFID tag attached to the lead wire.
Figure 7:
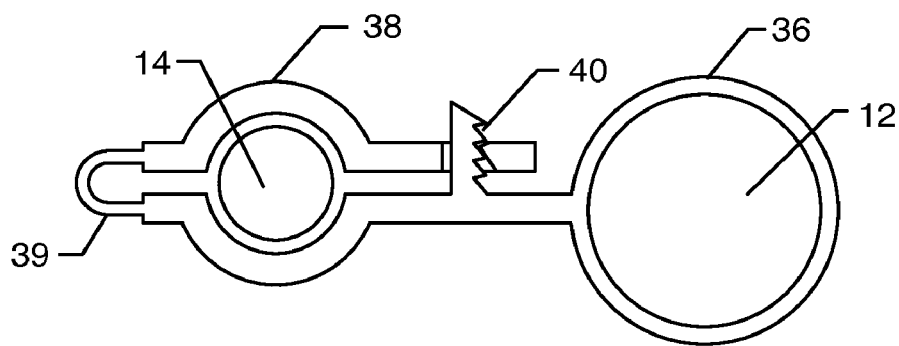
FIG. 7 is a sectional view of an embodiment of a clamp device with a ratchet mechanism.
Figure 8:
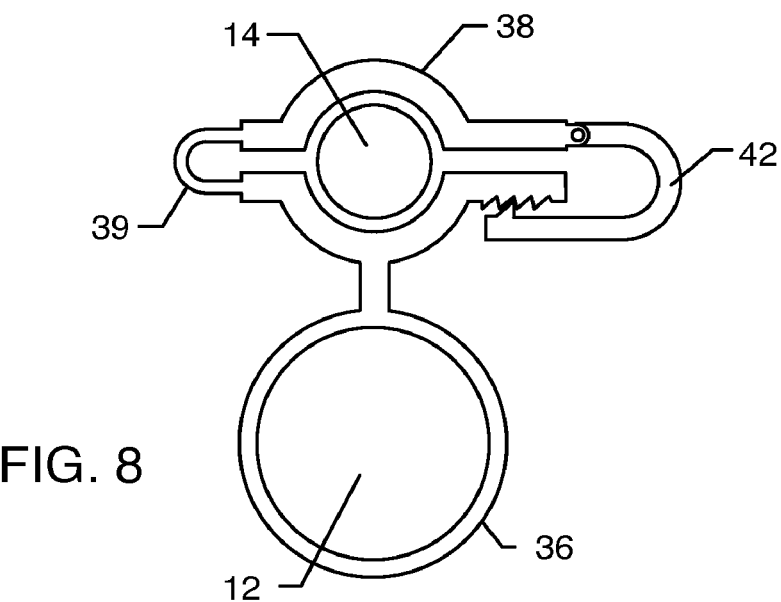
FIG. 8 is a sectional view of another embodiment of a clamp device with a clip mechanism.
Figure 9:
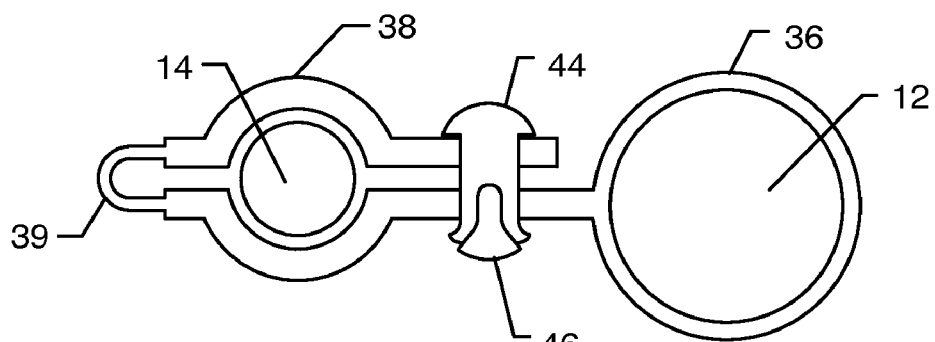
FIG. 9 is a sectional view of another embodiment of a clamp device with a rivet mechanism.

In yet another embodiment, the RFID tag 12 may be placed within a hermetically sealed container 36 which is attached to the lead wire 14, such as by the clamshell/clamp device 38 illustrated in FIG. 6. The container 36 could also include a suture 26 or other connecting means attaching the container 36, with the RFID tag 12 therein, to the lead wire 14. For example, FIGS. 7-9 show examples of various connecting means. FIG. 7 illustrates how container 36 may include a clamshell device 38 comprised of two separate pieces connected by a flexible hinge 39 which capture the lead wire 14 and are brought towards one another and held in place through a ratchet mechanism 40. FIG. 8 shows another embodiment of the clamshell device 38 with a clip mechanism 42 as a connecting means. FIG. 9 shows another embodiment of the clamshell device 38 with a rivet connecting means. Rivet 44 is inserted through an aperture and a plug 46 deforms the opposite end such that it permanently secures the two pieces of the clamshell device 38 together.

In FIGS. 7, 8 and 9, the ratchet, clip and/or rivet mechanisms must be manufactured of biocompatible materials. These could be various plastics, polymers, stainless steel, titanium or other biocompatible materials that are well known in the prior art. It will also be appreciated that surfaces should be rounded as much as possible. In other words, in FIG. 7, the sharp point of the ratchet mechanism would typically be rounded (not shown) so that it does not irritate local tissues. Any of the designs shown in FIGS. 4, 6, 7, 8 or 9 may include one or more suture tabs 35 as shown in FIG. 5. In addition, any of the designs illustrated in FIGS. 5, 6, 7 8 or 9 may include suture rings/channels 28 as previously illustrated in FIG. 4.

The association of the RFID tag 12 with the lead wires 14 and 16 enable the physician to determine the presence of the lead wires 14 and 16, whether or not attached to an IMD or subsequently abandoned. As described above, this can be very useful information to the physician in determining care of the patient. For example, symptoms of the patient may be linked to the lead wires themselves, such as lead wires migrating to an undesirable location. Alternatively, the presence of the lead wires 14 and 16 may contraindicate use of MRI or the like.

Figure 10:
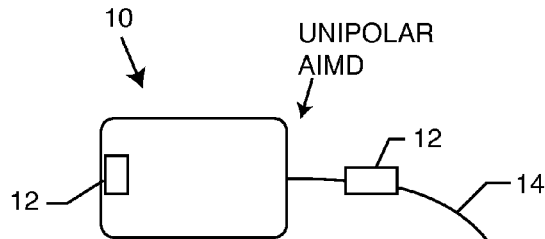
FIG. 10 is a diagram of a unipolar implantable medical device having RFID tags associated therewith.

With reference now to FIG. 10, a unipolar IMD 10 is shown with a single lead wire 14 extending therefrom. An RFID tag is associated with the lead 14, in this case intermediate the IMD 10 and the distal electrode 48. An RFID tag 12 may also be associated with the IMD itself, as illustrated.

On all new products, the RFID tag 12 is preferably directly attached to the device or included within the device/product during its manufacture. The RFID tag 12 may be placed within a hermetically sealed container 36 which is attached to the lead 14 (or any other component), such as by a clamshell device 38 including a suture ring 28, suture tab 35, ratchet 40, clip 42, rivet 44 or any other suitable means. Optimally, some sort of clamshell/hinged or two-part circumferential locking mechanism will be easily attachable to historic leads without initial RFID mechanisms; whereas all new leads will include a pre-mounted repositionable sleeve-like mechanism that can be firmly fixed in place at the ideal location on the lead body after the distal electrodes have been appropriately positioned within the heart or other desired terminal location. The RFID tag-carrying sleeve-like device may include a screw within a screw plastic compression or side lock/reversible rivet type mechanism for providing ideal compression of the lead insulation without introducing inappropriate forces that promote lead insulation deterioration during exposure to body fluids as typical of many polyurethane materials used for insulating CRMD leads in the past. The twist or clip lock mechanism will avoid the need for a potentially high risk encircling of the lead body with suture material and also reliably prevent the lead body from inward or outward migration at the point of deep tissue entry or other fixation site. Outward and on occasion, inward migration of the lead body resulting in an electrode displacement and other problems are common and obvious disadvantages of current suture/suture sleeve fixation approaches and techniques.

Figure 11:
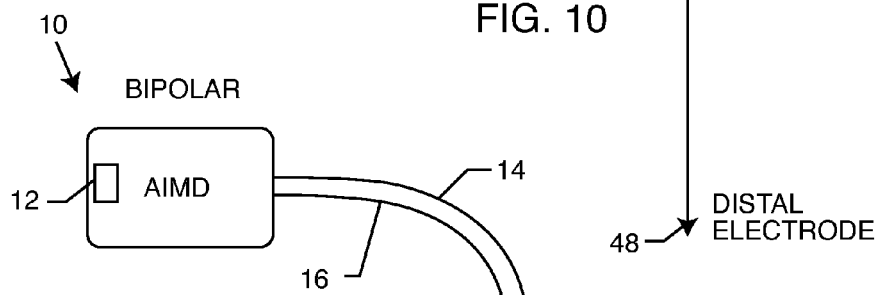
FIG. 11 is a diagram similar to FIG. 7, illustrating a bipolar IMD system.
Figure 12:
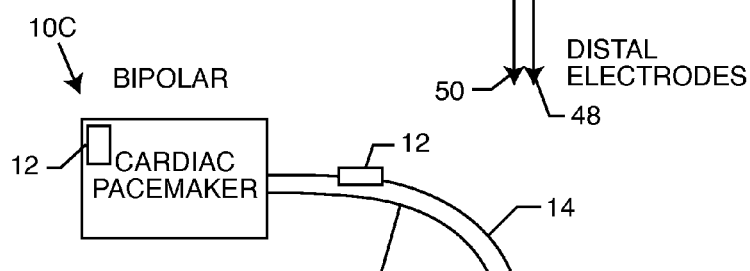
FIG. 12 is a diagram similar to FIG. 11, illustrating a bipolar lead wire system and a distal Tip and Ring typically used in a cardiac pacemaker.

FIG. 11 is very similar to FIG. 10 except that it is a bipolar system. In this case, the electric circuit return path is between the two distal electrodes 48 and 50. In the case of a cardiac pacemaker 10C, this would be known as a bipolar lead wire system with one of the electrodes known as the distal Tip 52 and the other electrode which would float in the blood pool known as the Ring 54 (see FIG. 12). In contrast, the electrical return path in FIG. 10 is between the distal electrode 40 through body tissue to the conductive housing of the implantable medical device 10.

In all of these applications, the patient could be exposed to the fields of an MRI scanner or other powerful emitter used during a medical diagnostic procedure. Currents that are directly induced in the lead wire system 14 can cause heating by $I^2R$ losses in the lead wire system or by heating caused by current flowing in body tissue. If these currents become excessive, the associated heating can cause damage or even destructive ablation to body tissue.

The distal Tip 52 is designed to be implanted into or affixed to the actual myocardial tissue of the heart. The Ring 54 is designed to float in the blood pool. Because the blood is flowing and is thermally conductive, the Ring 54 structure is substantially cooled. In theory, however, if the lead curves, the Ring 54 could also touch and become encapsulated by body tissue. The distal Tip 52, on the other hand, is always thermally insulated by surrounding body tissue and can readily heat up due to the RF pulse currents of an MRI field. In accordance with the present invention, RFID tags 12 are associated with at least the IMD 10 or a lead wire 14 extending therefrom. Preferably, an RFID tag is associated with both the IMD 10 as well as all lead wires 14, etc. extending therefrom. In this manner, as described above, the physician can interrogate the RFID tag 12 and be provided information regarding the IMD 10, lead wire system, patient, etc.

In a particularly preferred embodiment, a tank circuit or bandstop filter 56 is associated with the IMD 10 and lead wire system 14 such that the presence of the MRI signal or static field does not heat up the lead wires 14, 16, etc. leading to tissue damage or damage to the implantable device, sensors, lead systems, etc.

Figure 13:
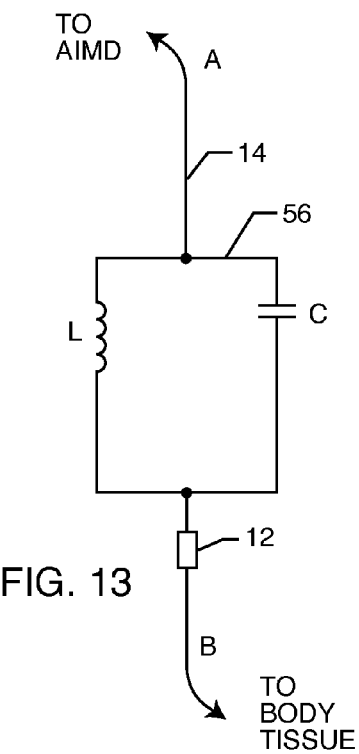
FIG. 13 is a schematic diagram showing a parallel combination of an inductor L and a capacitor C illustrating a bandstop filter, which can be placed in the lead wire systems of FIGS. 10-12.

FIG. 13 is a schematic diagram showing a parallel combination of an inductor L and a capacitor C to be placed in the lead wire systems 14 previously described. This combination forms a parallel tank circuit or bandstop filter 56 which will resonate at a particular frequency ($f_r$). US 2007-0112398 A1 discloses various bandstop filter structures and applications, any of which can be incorporated into the present invention.

The general principle behind all of the bandstop filter structures is the parallel combination of an inductor L and a capacitor C having values selected such that the filter 56 resonates at the particular frequency of the pulsed RF field associated with the MRI. In FIG. 10, the bandstop filter 48 is illustrated as being between the IMD and the distal electrode inserted into the body tissue. However, it will be appreciated that the bandstop filter 56 can be placed immediately adjacent to the IMD, immediately adjacent to the distal electrodes 48, or anywhere along the length of the lead wire 14 therebetween. In fact, multiple bandstop filters 56 can be implemented such that one bandstop filter 56 is disposed adjacent to the IMD 10, and the other adjacent to the distal electrode 48. The bandstop filter 56 will resonate at a particular MRI frequency, rendering the IMD and lead wire system (whether associated with an IMD or abandoned) compatible with that particular MRI frequency. This information is included in the RFID tag 12, so that the physician will know that the patient can have an MRI at that frequency even though there are implantable lead wires 14, 16.

MRI systems vary in static field strength from 0.5 Tesla all the way up to 3 Tesla with newer research machines going much higher. This is the force of the main static magnetic field. The frequency of the pulsed RF field associated with MRI is found by multiplying the static field in Tesla times 42.45. Accordingly, a 3 Tesla MRI system has a pulsed RF field of approximately 128 MHz. If the values of the inductor L and the capacitor C are selected properly, one could obtain a parallel bandstop filter resonant frequency of 128 MHz. For a 1.5 Tesla MRI system, the RF pulse frequency is 64 MHz.

Figure 14:
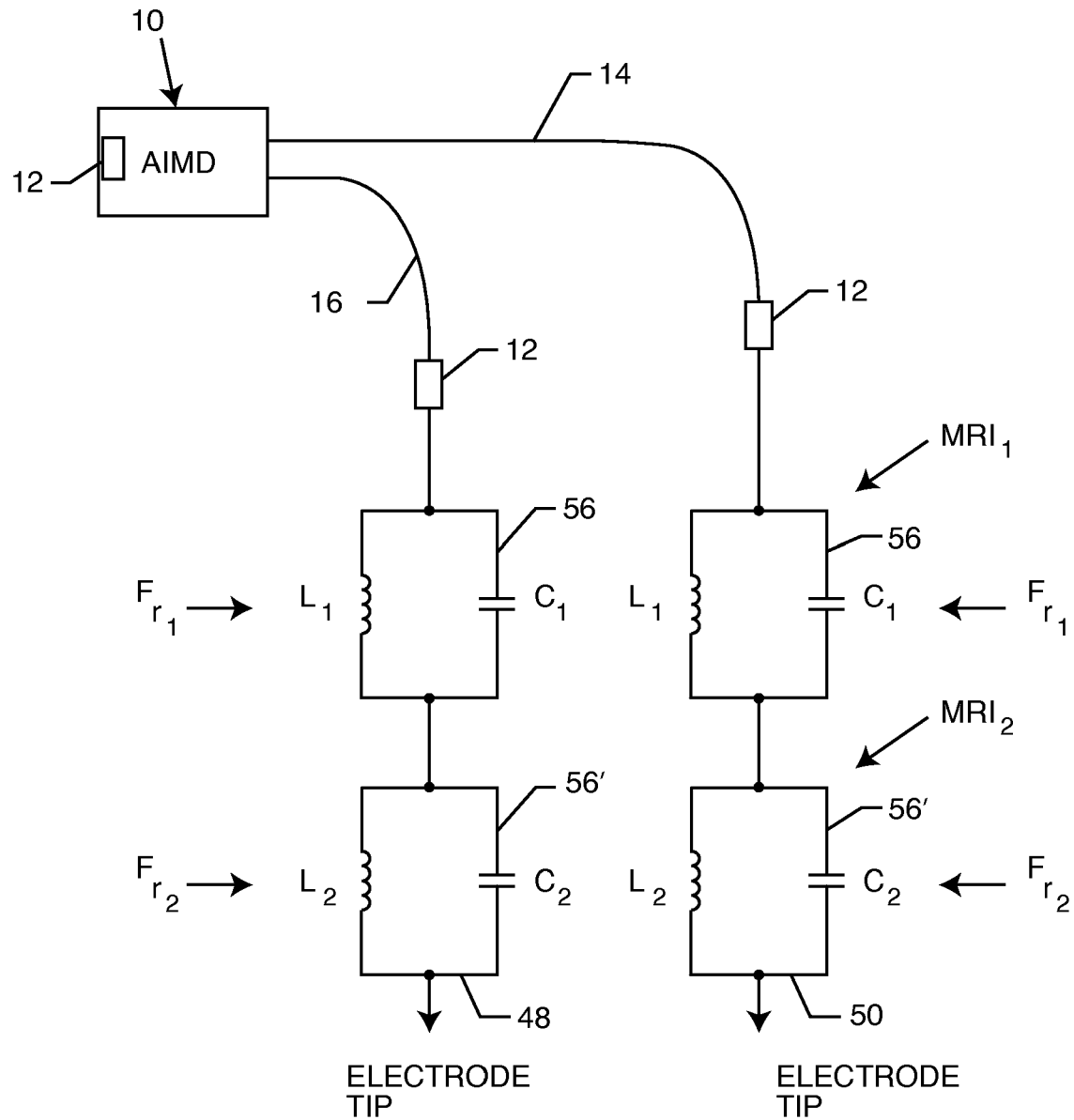
FIG. 14 is a schematic diagram similar to FIG. 13, but illustrating an IMD with multiple lead wires, each lead wire incorporating multiple bandstop filters.

FIG. 14 is the bipolar system of FIG. 11 redrawn to show two bandstop filters 56 in each lead wire 14, 16. In this case, there is a tank circuit $F_{r1}$ consisting of $L_1$ and $C_1$ in both of the bipolar lead wires 14, 16, which is designed to resonate at one selected frequency. For example, for a 1.5 Tesla MRI system, this would be 64 MHz. These are then placed in series with a second set of bandstop filters 56' which are designed to resonate at $F_{r2}$. These consist of $L_2$, $C_2$ parallel inductor capacitor combinations. For example, these could be designed for operation in a 3 Tesla MRI system and would therefore be designed to resonate at 128 MHz. In this way, currents would be blocked from both types of MRI systems. It will be appreciated that there is no limit to the number of bandstop filters 56 which can be utilized so as to make the lead wire system and IMD compatible with different MRI systems. Of course, the trade off here is that the distal electrodes 48, 50 would be physically elongated due to the additional components necessary. The RFID tags 12, which are preferably associated with each lead wire 14, 16, etc., but at a minimum associated with the entire lead wire system, includes information relating to the bandstop filters incorporated in the lead system and thus the MRI compatibility of the lead wire system. Thus, using the interrogator 20 illustrated and described above, the physician and emergency health care personnel can determine the presence of implanted medical devices 10, the presence of active or abandoned lead wire systems, and their compatibility, if any, with MRI systems. This can be done in a fairly quick manner so that the proper diagnosis and treatment, which may include MRI scans, can be given by the physician.

Although several embodiments have been described in detail for purposes of illustration, various modifications may be made without departing from the scope and spirit of the invention.

What is claimed is:

1. An identification device for an implantable lead, comprising:
   a) an implantable sleeve associated with the implantable lead; and
   b) a radio frequency identification device (RFID) tag associated with the sleeve, the RFID tag having information relating to the implantable lead, its associated lead system, or an associated implantable medical device (IMD).

2. The device of claim 1, wherein the RFID tag is hermetically sealed within the sleeve.

3. The device of claim 1 or 2, wherein the sleeve is selectively fixed along a length of the lead.

4. The device of claim 3, wherein the sleeve comprises a loop forming an aperture, where the aperture captures a portion of the lead therein.

5. The device of claim 4, wherein the sleeve comprises a suture channel for secure attachment to the lead.

6. The device of claim 4, wherein the sleeve comprises a suture tab.

7. The device of claim 4, wherein the sleeve comprises a clamp device including a crimp, a clamp, a ratchet, clip, or rivet mechanism or clamshells configured to cooperatively capture the lead.

8. The device of claim 3, wherein the sleeve is integrally formed as part of the lead.

9. The device of claim 8, wherein the sleeve is disposed between a lead conductor and an insulated lumen.

10. The device of claim 1, including an external interrogator for identifying information contained within the REID tag when brought into close proximity.

11. The device of claim 10, wherein the interrogator is operably coupled to an access or reading device which can relay the information to a physician or access a database to retrieve a patient's information.

12. The device of claim 10, wherein the information comprises a patient's name, a date of birth, a patient hospital identification number, a physician name, a medical history, a name and number of implanting physician, an implant date, an implant hospital, a lead model or serial numbers, a lead's position, a defibrillation energy, a HV impedance, a P/R wave amplitude slew rate, a pacing threshold, a pulse pacing width, a pacing impedance, or a threshold current.

13. An identification device for an implantable lead, comprising:
   a) an implantable sleeve associated with the implantable lead wherein the sleeve is selectively fixed along a length of the lead;
   b) a radio frequency identification device (RFID) tag hermetically sealed within the sleeve, the RFID tag having information relating to the implantable lead, its associated lead system, or an associated implantable medical device (IMD); and
   c) an external interrogator for identifying information contained within the RFID tag when brought into close proximity.

14. The device of claim 13, wherein the information comprises a patient's name, a date of birth, a patient hospital identification number, a physician name, a medical history, a name and number of implanting physician, an implant date, an implant hospital, a lead model or serial numbers, a lead's position, a defibrillation energy, a HV impedance, a P/R wave amplitude slew rate, a pacing threshold, a pulse pacing width, a pacing impedance, or a threshold current.

15. The device of claim 13, wherein the sleeve comprises a loop forming an aperture, where the aperture captures a portion of the lead therein and is selectively fixed along a length of the lead.

16. The device of claim 13, wherein the sleeve comprises a crimped clamp device, a ratchet, clip, or rivet mechanism, or clamshells configured to cooperatively capture the lead.

17. The device of claim 16, wherein the sleeve comprises a suture tab.

18. The device of claim 16, wherein the sleeve comprises a suture channel.

19. The device of claim 13, wherein the sleeve is integrally formed as part of the lead so that the sleeve is disposed between a lead conductor and an insulated lumen.

* * * * *